US012788429B2

(12) United States Patent
Helebert et al.

(10) Patent No.: US 12,788,429 B2
(45) Date of Patent: Nov. 10, 2026

(54) TISSUE-REMOVING CATHETER WITH A COUPLED INNER LINER

(71) Applicant: Medtronic Vascular, Inc., Santa Rosa, CA (US)

(72) Inventors: Rebecca Marie Helebert, Galway (IE); Thomas P. Hayden, Turloughmore (IE); Laura A. Pilkington, Birr (IE); Eoin J. Walsh, Doughiska (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 114 days.

(21) Appl. No.: 19/015,527

(22) Filed: Jan. 9, 2025

(65) Prior Publication Data

US 2025/0248733 A1 Aug. 7, 2025

Related U.S. Application Data

(63) Continuation of application No. 17/806,123, filed on Jun. 9, 2022, now Pat. No. 12,201,318.

(Continued)

(51) Int. Cl.
*A61B 17/00* (2006.01)
*A61B 17/32* (2006.01)

(Continued)

(52) U.S. Cl.
CPC ................ *A61B 17/320758* (2013.01); *A61B 17/32075* (2013.01); *A61B 17/320783* (2013.01);

(Continued)

(58) Field of Classification Search
CPC ...... A61B 17/32002; A61B 17/320016; A61B 17/3207; A61B 17/320758;

(Continued)

(56) References Cited

U.S. PATENT DOCUMENTS

| | | | | |
|---|---|---|---|---|
| 6,626,923 B1 | 9/2003 | Wyzgala | | |
| 2011/0087254 A1* | 4/2011 | Welty ............. | A61B 17/320758 606/159 | |

(Continued)

FOREIGN PATENT DOCUMENTS

WO WO2013123007 A1 8/2013

OTHER PUBLICATIONS

Communication pursuant to Article 94(3), from EP Application No. 22183579.6 dated Aug. 21, 2024, 4 pages.

*Primary Examiner* — Tan-Uyen T Ho
*Assistant Examiner* — Lindsey R. Rivers
(74) *Attorney, Agent, or Firm* — Stinson LLP

(57) ABSTRACT

The present disclosure provides a tissue-removing catheter for removing tissue in a body lumen that includes an elongate body, a handle, tissue-removing element, liner assembly, and coupling assembly. The elongate body is sized and shaped to be received in the body lumen. The tissue-removing element is mounted on a distal end portion of the elongate body and removes tissue as rotated by the elongate body. The liner assembly defines a guidewire lumen. The coupling assembly is coupled to the liner assembly with a first orientation and a second orientation relative to the coupling assembly. The first orientation permits distal movement of the liner assembly relative to the coupling assembly prior to rotation of the elongate body to rotate the tissue-removing element. The second orientation is relative to the coupling assembly after rotation of the elongate body to prevent distal movement of the liner assembly relative to the coupling assembly.

16 Claims, 16 Drawing Sheets

Related U.S. Application Data

(60) Provisional application No. 63/225,863, filed on Jul. 26, 2021.

(51) Int. Cl.
*A61B 17/3207* (2006.01)
*A61B 17/22* (2006.01)

(52) U.S. Cl.
CPC ............... *A61B 2017/00292* (2013.01); *A61B 2017/00398* (2013.01); *A61B 2017/320064* (2013.01); *A61B 2017/320741* (2013.01); *A61B 2017/320791* (2013.01)

(58) Field of Classification Search
CPC .. A61B 17/320783; A61B 2017/00398; A61B 2017/00991; A61B 2017/320032
See application file for complete search history.

(56) References Cited

U.S. PATENT DOCUMENTS

| | | | |
|---|---|---|---|
| 2012/0109171 | A1 | 5/2012 | Zeroni et al. |
| 2020/0155194 | A1 | 5/2020 | Schneider |
| 2020/0360047 | A1 | 11/2020 | Kelly et al. |

* cited by examiner

TISSUE-REMOVING CATHETER WITH A COUPLED INNER LINER

STATEMENT OF RELATED CASES

This application is a continuation of U.S. Non-Provisional patent application Ser. No. 17/806,123, filed on Jun. 9, 2022, which claims the benefit of U.S. Provisional Patent Application Ser. No. 63/225,863, filed on Jul. 26, 2021, the entire content of each is hereby incorporated by reference.

FIELD

The present disclosure generally relates to a tissue-removing catheter, and more particular, to a coupled inner liner of a tissue-removing catheter.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters typically employ a rotating element which is used to abrade or otherwise break up the unwanted tissue.

BRIEF SUMMARY

In one aspect, the present disclosure provides a tissue-removing catheter for removing tissue in a body lumen. The tissue-removing catheter includes an elongate body, a handle, a tissue-removing element, a liner assembly, and a coupling assembly. The elongate body has an axis, a proximal end portion and a distal end portion spaced apart from the proximal end portion along the axis. The elongate body is sized and shaped to be received in the body lumen. The handle is mounted to the proximal end portion of the elongate body. The handle includes a housing that encloses components operable to cause rotation of the elongate body. The tissue-removing element is mounted on the distal end portion of the elongate body. The tissue-removing element removes tissue as the tissue-removing element is rotated by the elongate body within the body lumen. The liner assembly defines a guidewire lumen. The coupling assembly is coupled to the liner assembly such that the liner assembly has a first orientation and a second orientation relative to the coupling assembly. The first orientation permits distal movement of the liner assembly relative to the coupling assembly prior to rotation of the elongate body to rotate the tissue-removing element. The second orientation is relative to the coupling assembly after rotation of the elongate body to prevent distal movement of the liner assembly relative to the coupling assembly.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Corresponding reference characters indicate corresponding parts throughout the drawings.

DETAILED DESCRIPTION

Figure 1:
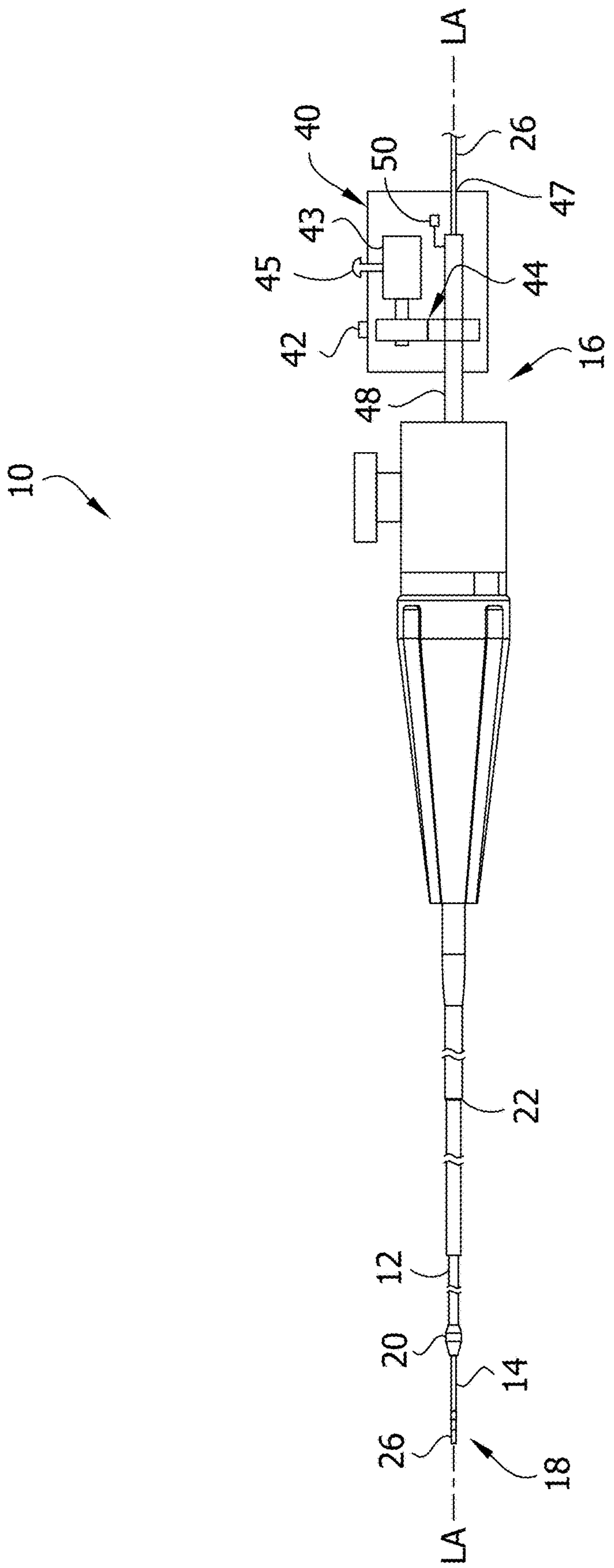
FIG. 1 is a schematic illustration of a catheter of the present disclosure.

Referring to the drawings, and in particular FIG. 1, a rotational tissue-removing catheter for removing tissue in a body lumen is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in a blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 2:
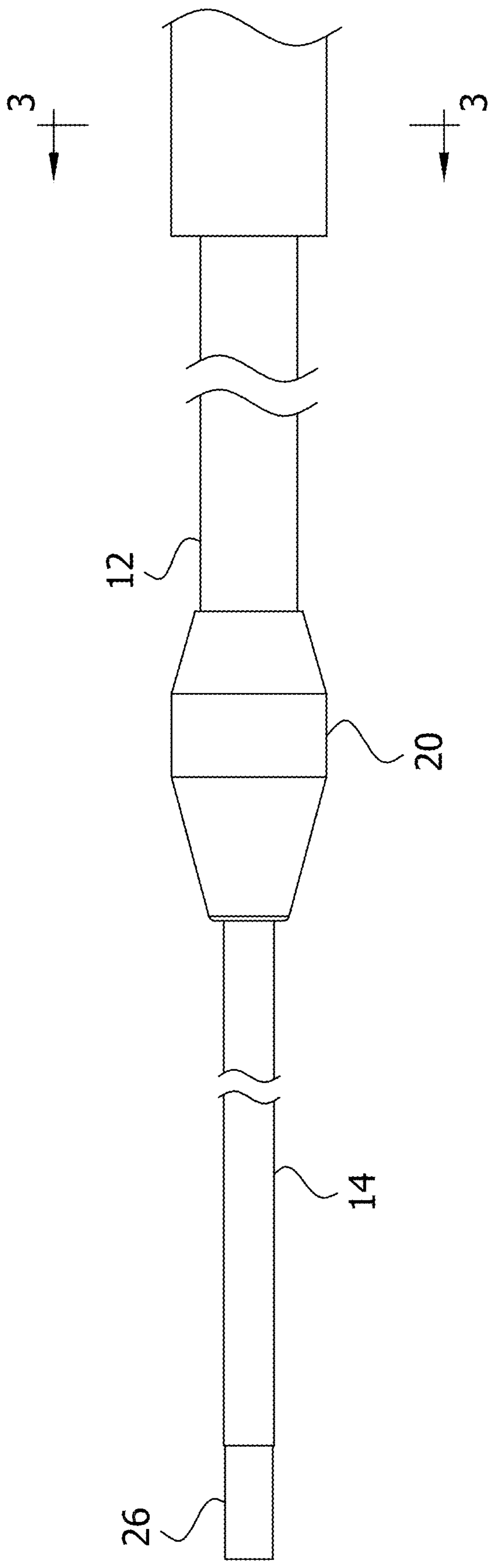
FIG. 2 is an enlarged elevation of a distal end portion of the catheter.
Figure 3:
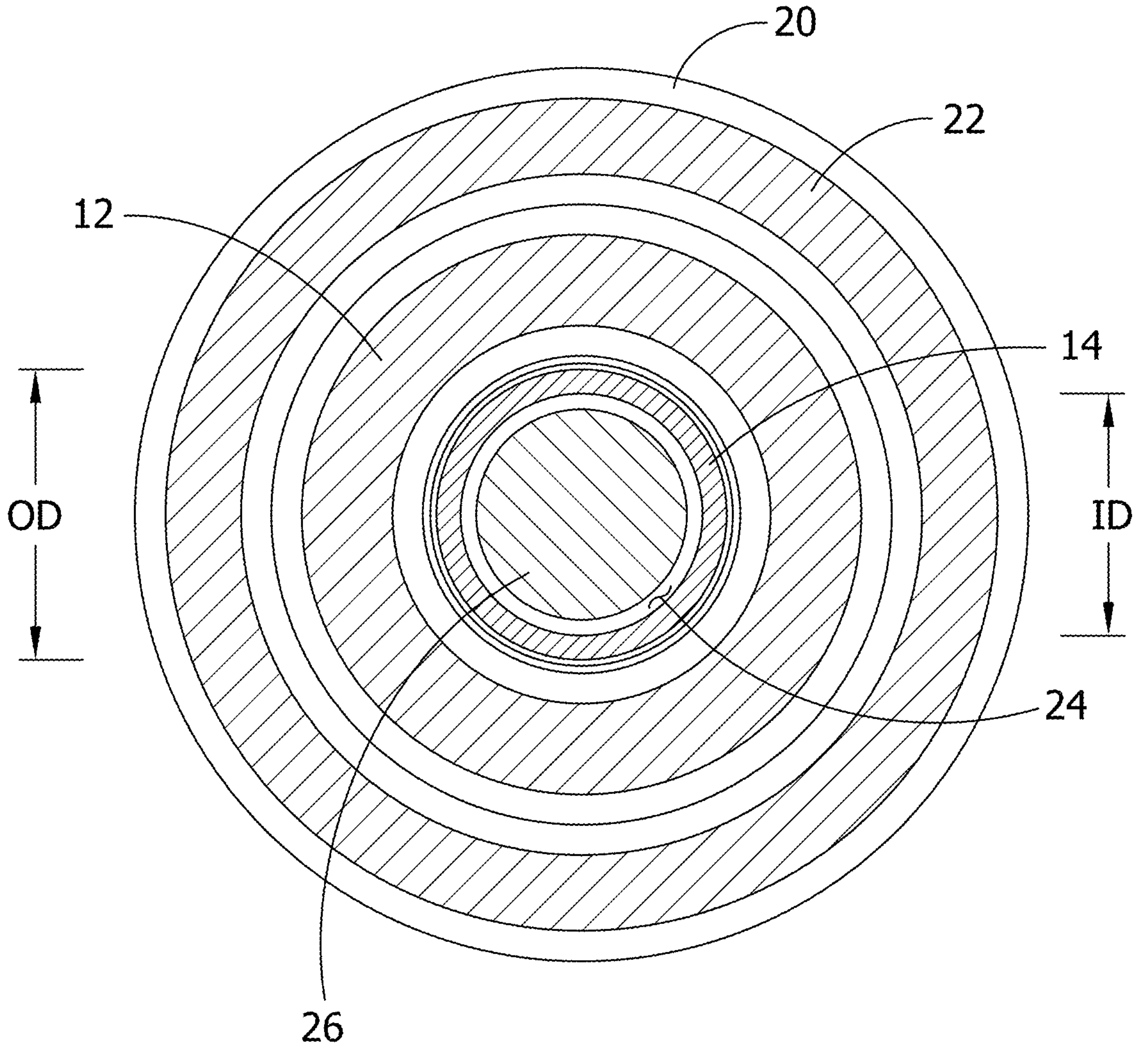
FIG. 3 is a cross section taken through line 3-3 in FIG. 2.

Referring to FIGS. 1-3, the catheter 10 comprises an elongate drive coil 12 (broadly, an elongate body) disposed around an elongate inner liner 14. The drive coil 12 and inner liner 14 extend along a longitudinal axis LA of the catheter 10 from a proximal end portion 16 to a distal end portion 18 of the catheter. A tissue-removing element 20 is disposed on a distal end of the drive coil 12 and is configured for rotation to remove tissue from a body lumen as will be explained in greater detail below. An isolation sheath 22 is disposed around the drive coil 12. The drive coil 12 and the inner liner 14 are both configured to translate relative to the isolation sheath 22. The catheter 10 is sized and shaped for insertion into a body lumen of a subject. The isolation sheath 22 isolates the body lumen from at least a portion of the drive coil 12 and inner liner 14. The inner liner 14 defines a guidewire lumen 24 (FIG. 3) for slidably receiving a guidewire 26 therein so that the catheter 10 can be advanced through the body lumen by traveling along the guidewire. The guidewire can be a standard 0.014-inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends along an entire working length of the catheter 10. In one embodiment, the overall working length of the catheter 10 may be between about 135 cm (53 inches) and about 142 cm (56 inches). In use, the guidewire 26 may extend about 40 mm (1.6 inches) past a distal end of the inner liner 14.

Referring to FIGS. 1 and 4-7, the catheter 10 further comprises a handle 40 secured at a proximal end of the isolation sheath 22. The handle 40 comprises a housing 41 that supports components of the handle. The housing 41 has a generally elongate egg shape and includes a plurality of housing sections secured together to enclose internal components of the handle 40. In the illustrated embodiment, the housing 41 includes a bottom housing section 41A, a middle housing section 41B secured to the top of the bottom housing section, and a top housing section 41C secured to the top of the middle housing section. In one embodiment, the bottom housing section 41A is removable from the middle housing section 41B to provide access to the components of the handle 40 in the interior of the housing 41 by a user. It will be understood that the housing 41 can have other shapes and configurations without departing from the scope of the disclosure.

The housing 41 supports an actuator 42 (e.g., a lever, a button, a dial, a switch, or other device) configured for selectively actuating a motor 43 disposed in the handle to drive rotation of the drive coil 12, and the tissue-removing element 20 mounted at the distal end of the drive coil. The motor 43 is configured to rotate the drive coil 12 and tissue-removing element 20 at speeds of greater than about 80,000 RPM. In one embodiment, the motor 43 rotates the drive coil 12 and tissue-removing element 20 between about 10,000 and about 110,000 RPM. The motor 43 is coupled to the drive coil 12 by a gear assembly 44 and drive assembly 48 supported within the housing 41. The gear assembly 44 comprises a gearbox housing 55 that mounts and at least partially encloses a pair of gears for transferring the rotation of a shaft of the motor 43 to the drive coil 12.

Figure 6:
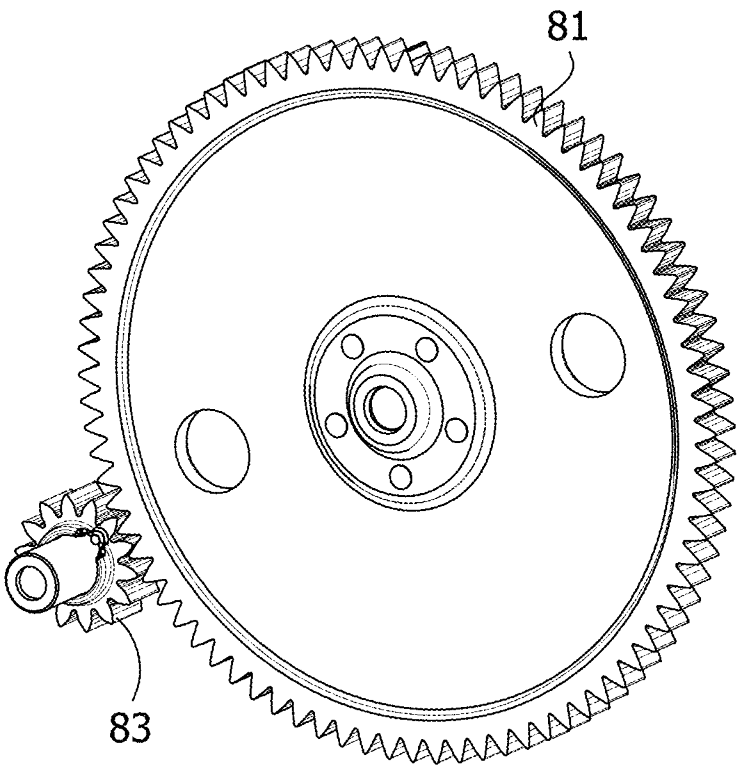
FIG. 6 is a perspective of gears of a gear assembly in the handle.
Figure 7:
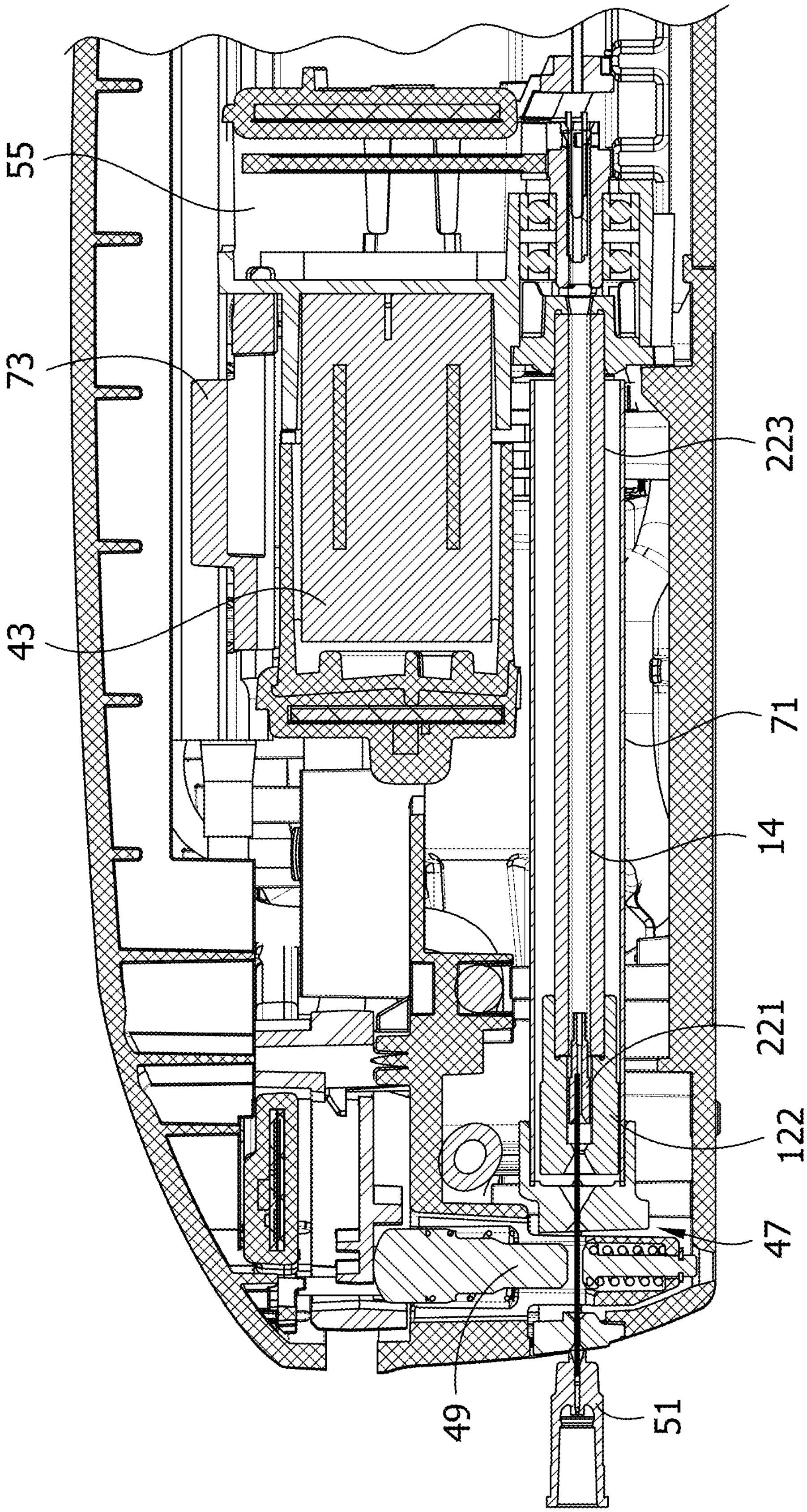
FIG. 7 is a fragmentary longitudinal cross section of the handle.

The motor 43 is coupled to the drive coil 12 by a gear assembly 44 and drive assembly 48 supported within the housing 41. The gear assembly 44 comprises a gearbox housing 55 that mounts and at least partially encloses a pair of gears for transferring the rotation of a shaft of the motor 43 to the drive coil 12. The gearbox housing 55 includes a rear housing section 61 and a front housing section 63 formed integrally with the rear housing section such that the gearbox housing comprises a single housing structure (FIG. 7). A sleeve portion 69 of the gearbox housing is disposed generally below the front and rear housing sections 61, 63 and attaches to a distal end portion of a guide tube 223. The gearbox housing 55 attaches to a carriage or advancer frame 73 for moving the motor 43 and gear assembly 44 within the housing 41. In an embodiment, attaching the gearbox housing 55 to the distal end of the advancer frame 73 secures the motor 43 in the advancer frame so that the motor moves along with the advancer frame. The sleeve portion 69 also receives a portion of the drive assembly 48. A driver gear 81 is attached to the motor 43 such that the driver gear rotates with the motor shaft when the motor 43 is activated (FIG. 6). A driven gear 83 is in mesh with the driver gear 81 so that rotation of the driver gear causes the driven gear to rotate in the opposite direction. The drive assembly 48 attaches the driven gear 83 to the drive coil 12 so that the rotation of the driven gear causes the drive coil to rotate. A controller 50 may be provided in the handle 40. The controller 50 may be programmed to control operation of the catheter.

It is understood that other suitable actuators, including but not limited to touchscreen actuators, wireless control actuators, automated actuators directed by a controller, etc., may be suitable to selectively actuate the motor in other embodiments. In some embodiments, a power supply may come from a battery (not shown) contained within the handle 40. The battery can provide the current source for the guidewire detection circuit. In other embodiments, the power supply may come from an external source.

Figure 4:
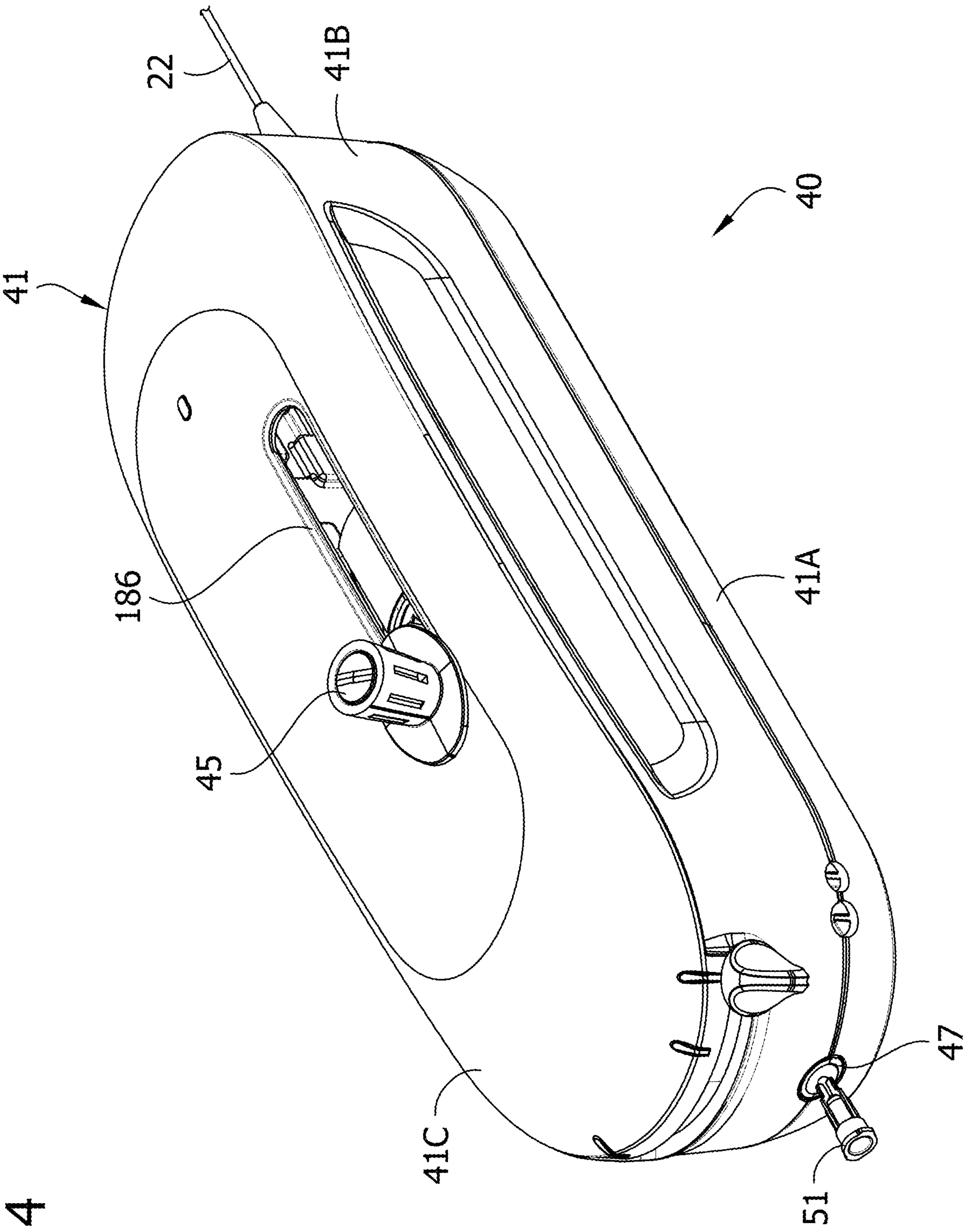
FIG. 4 is a top perspective of a handle of the catheter.
Figure 5:
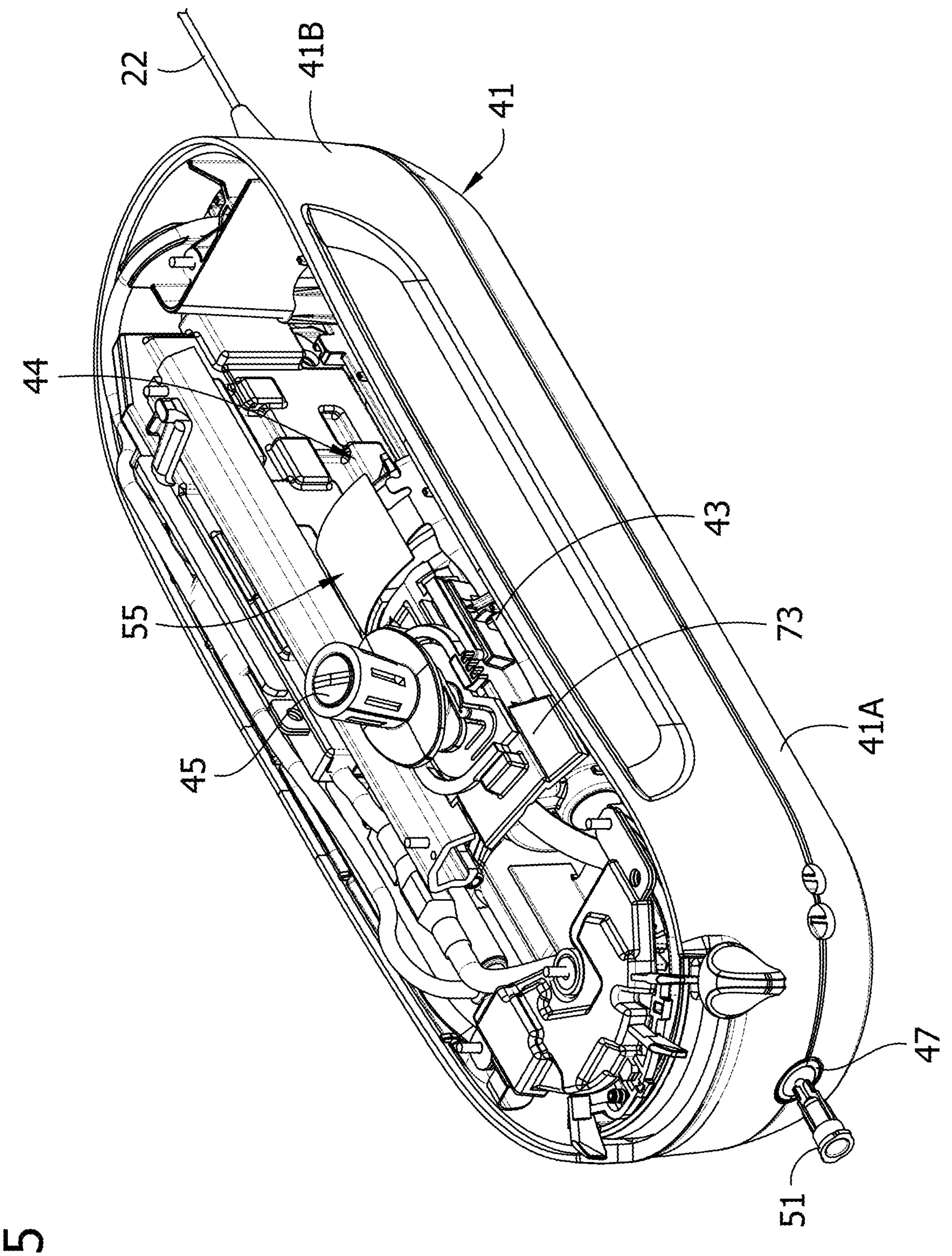
FIG. 5 is a top perspective of the handle with a top housing section removed.

Referring to FIGS. 1, 4, and 5, a slide or advancer 45 is positioned on the handle 40 and is operatively coupled to the inner liner 14 for movement of the inner liner relative to the handle to advance and retract the inner liner, drive coil 12, and tissue-removing element 20. The housing 41 of the handle 40 may define a slot 186 which limits the movement of the slide 45 relative to the handle. Thus, the length of the slot 186 determines the amount of relative movement between the inner liner 14 and the handle 40. In one embodiment, the slot has a length of about 70 mm (2.8 inches). The slide 45 is operatively attached to the advancer frame 73 so that movement of the slide causes movement of the advancer frame. The advancer frame 73 comprises an arch shaped body configured to slidingly receive the cylindrically shaped motor 43. Bearings (not shown) are mounted on the frame 73. The bearings engage the housing 41 so that the bearings can slide along the housing to facilitate movement of the frame 73 in the housing.

Figure 8:
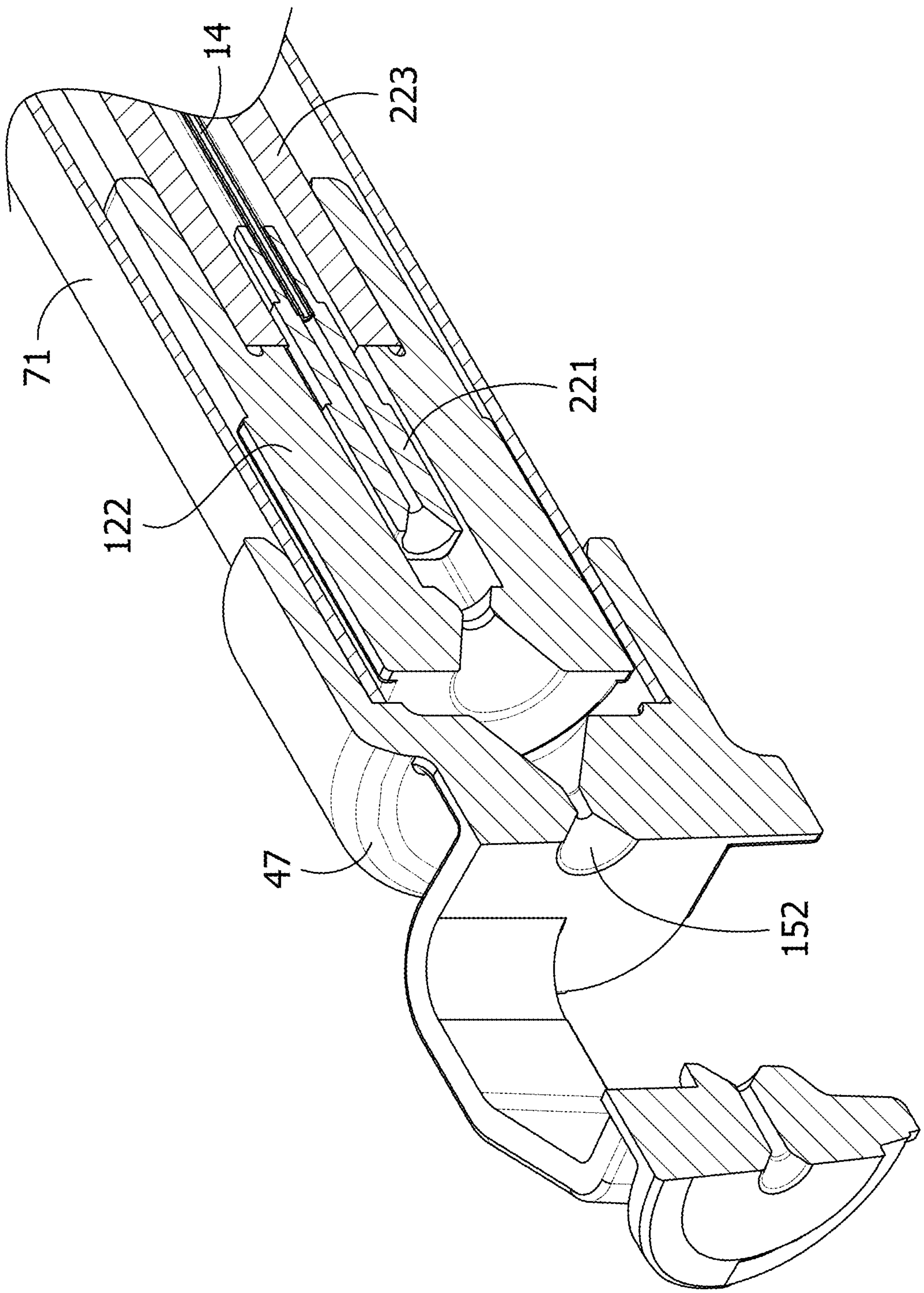
FIG. 8 is an enlarged fragmentary longitudinal cross section of internal components in the handle.
Figure 9:
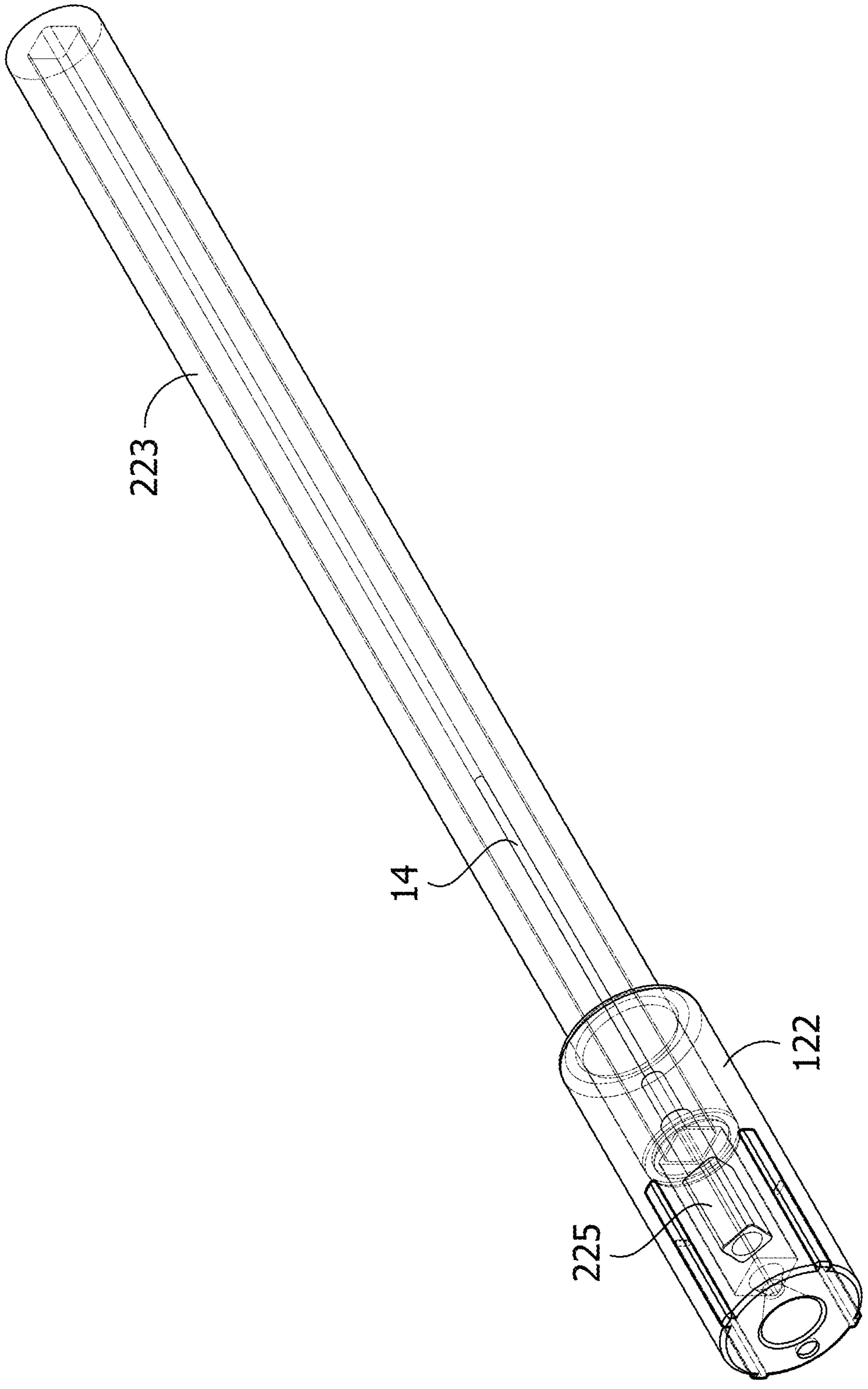
FIG. 9 is a perspective of a liner assembly received in a guide tube and coupling sleeve of the catheter.
Figure 10:
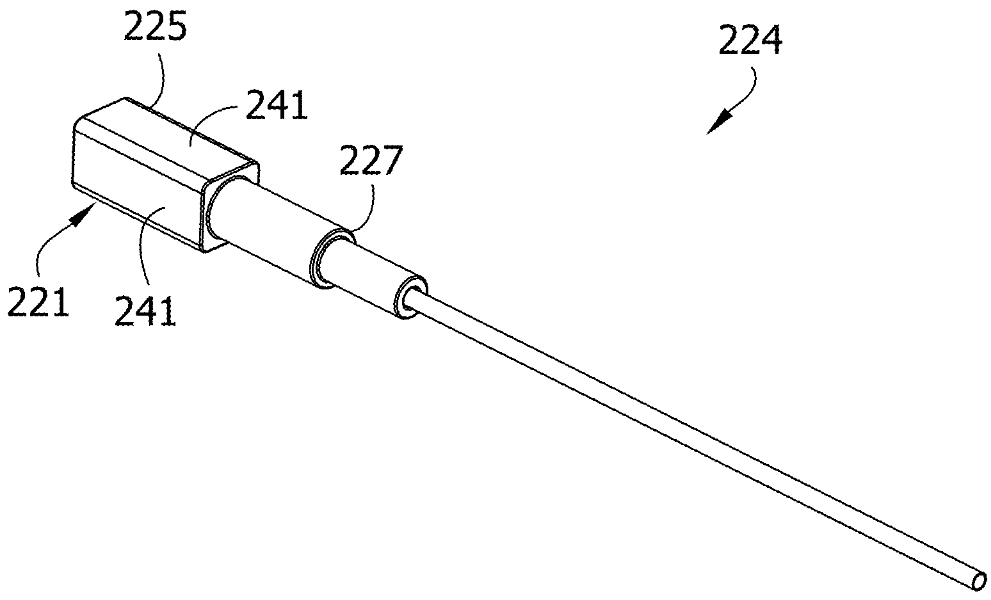
FIG. 10 is a fragmentary perspective of a liner assembly of the catheter.
Figure 11:
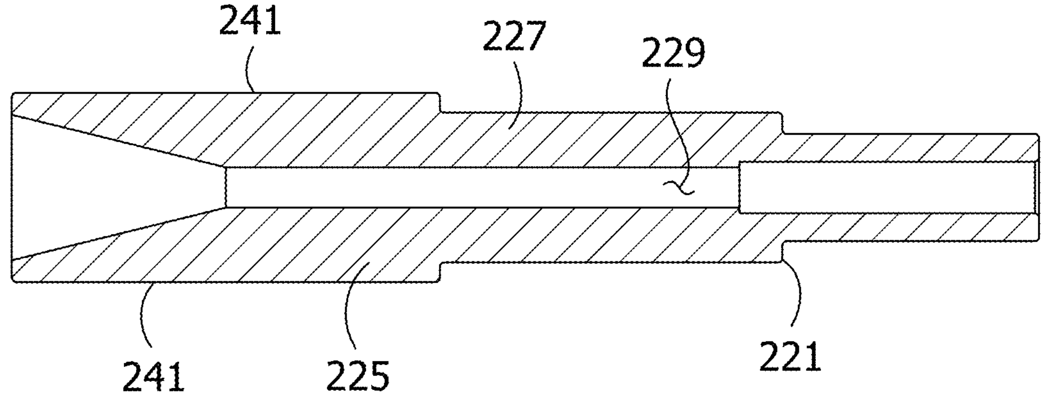
FIG. 11 is a cross section of a liner key of the liner assembly.

Referring to FIGS. 7-9, a guidewire port 47 is mounted on a proximal end of the buckle tube 71. In one embodiment, the guidewire port 47 is overmolded onto the buckle tube 71. Alternatively, the guidewire port 47 may be press fit onto the buckle tube 71. The guidewire port 47 provides structure in the handle 40 to support the guidewire at the proximal end of the handle. The guidewire port 47 defines an axial passage 152 (FIG. 8) through which the guidewire 26 extends.

Additionally, a guidewire lock 49 (FIG. 7) may be mounted on the guidewire port 47 to lock the guidewire 26 in place relative to the handle. The guidewire port 47 may also facilitate flushing of the inner liner 14 by passing a cannula 51 through the guidewire port and into the liner key to allow for flushing.

The guide tube 223 extends from the gearbox housing 55 at a distal end of the guide tube to a coupling sleeve 122 at a proximal end of the guide tube. The guide tube 223 is fixedly attached to the gear box housing 55, and the coupling sleeve 122 is fixedly attached to the guide tube 223. In one embodiment, the coupling sleeve 122 is press fit onto an outer surface of the proximal end of the guide tube 223. However, the coupling sleeve 122 can be attached to the guide tube 223 by any suitable means. The coupling sleeve 122 is movably received in the buckle tube 71. The engagement between the coupling sleeve 122 and the buckle tube 71 permits the coupling sleeve and guide tube 223 to translate relative to the buckle tube but prevents rotation of the coupling sleeve and guide tube 223 relative to the buckle tube. In particular, an interior passage in the buckle tube 71 provides sufficient clearance to receive the coupling sleeve 122 for axial movement but does not allow rotational movement of the coupling sleeve in the buckle tube. In one embodiment, axial translation of at least about 70 mm is permitted. It will be understood that the buckle tube 71 and coupling sleeve 122 may be operatively engaged by other means without departing from the scope of the disclosure.

Referring to FIGS. 8-11, a liner key 221 is attached to a proximal end of the liner 14 and is received in the coupling sleeve 122. As will be discussed in greater detail below, the liner key 221 is configurable to secure the liner key to the coupling sleeve 122. Thus, movement of the coupling sleeve 122 in the buckle tube 71 causes a corresponding movement of the liner key 221 when the liner key is in the coupled configuration. The liner key 221 can also facilitate flushing of the inner liner 14. The liner 14 extends distally from the liner key 221 through the guide tube 223. The liner 14 and liner key 221 may be broadly considered a liner assembly 224. In the illustrated embodiment, the liner key 221 comprises a locking member 225 and an elongate extension member 227 extending distally from a distal end of the locking member. A channel 229 (FIG. 11) extends through the liner key 221. The proximal end of the liner 14 is attached to the extension member 227 to secure the liner to the liner key 221. Thus, the liner key 221 and the liner 14 move together as a single unit. In one embodiment, the liner 14 is received in a portion of the channel 229 extending through the extension member 227. The liner 14 can be retained in the liner key 221 by any suitable means, including without limitation, glue, thermal bond, and mechanical bond. In the illustrated embodiment, the locking member 225 comprises a cuboidal structure comprising four flat surfaces 241. However, the locking member 225 may have other shapes without departing from the scope of the disclosure. In one embodiment, the locking member 225 has a non-circular or non-rounded exterior shape. It is envisioned that the liner key 221, guide tube 223, and buckle tube 71 can have other configurations for permitting relative translation and preventing relative rotation. In an embodiment, any suitable materials may be used for the liner key 221, guide tube 223, and buckle tube 71. For example, the liner key 221, can be formed from Peek, Polyoxymethylene (POM), or polycarbonate (PC).

Figure 12A:
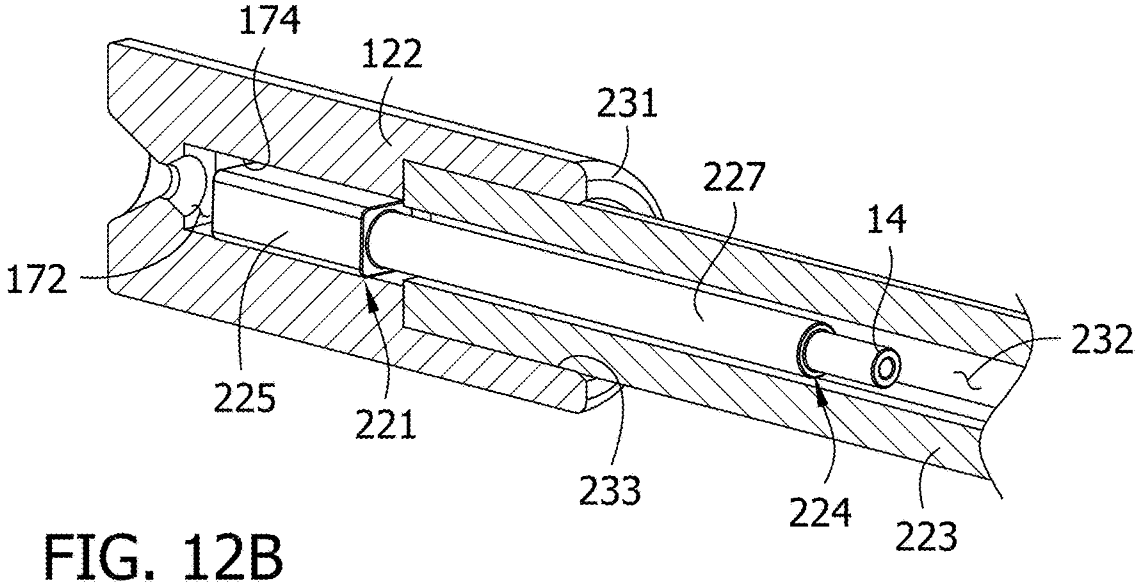
FIG. 12A is a fragmentary longitudinal cross section of the guide tube, coupling sleeve, and liner assembly, showing the liner assembly in a first orientation.
Figure 12B:
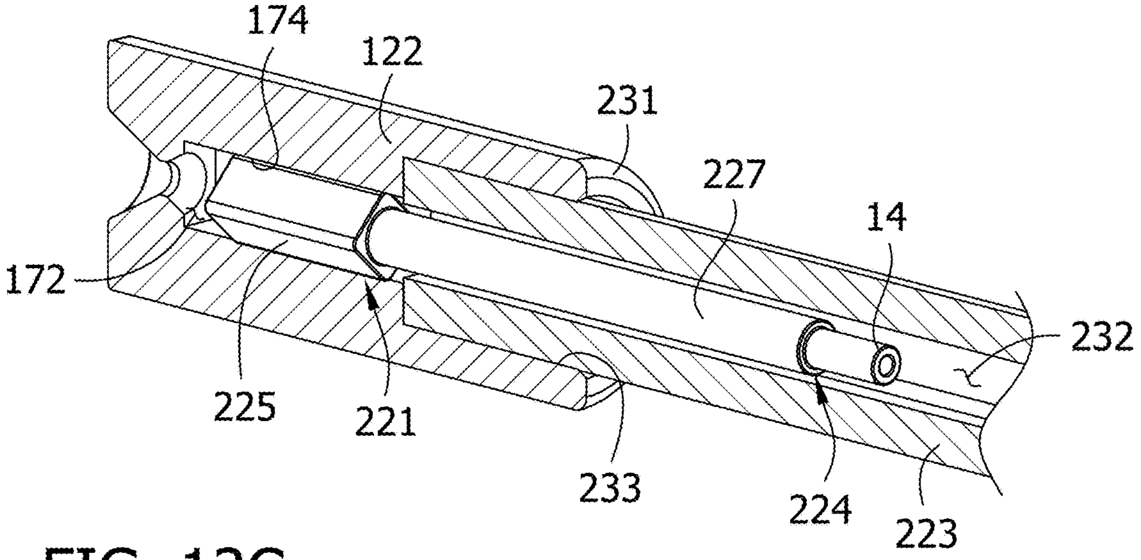
FIG. 12B is a fragmentary longitudinal cross section of the guide tube, coupling sleeve, and liner assembly, showing the liner assembly in a second orientation.
Figure 12C:
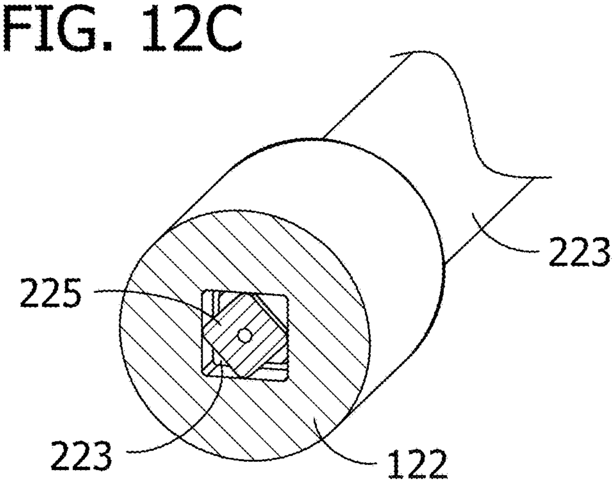
FIG. 12C is fragmentary perspective of the guide tube, coupling sleeve, and liner assembly showing the liner assembly in the second orientation.

Referring to FIGS. 12A-12C, to assemble the liner assembly 224 in the catheter 10, the liner assembly is inserted through the guide tube 223 and into a proximal end 231 of the coupling sleeve 122 to secure the liner assembly to the coupling sleeve. In particular, the liner assembly 224 is first inserted through the guide tube 223 where the cuboidal shape of the locking member 225 of the liner key 221 is aligned with a rectangular passage 232 in the guide tube to facilitate insertion of the liner assembly through the guide tube and prevent rotation of the liner key relative to the guide tube. The liner key 221 is then inserted past a proximal opening 233 in the coupling sleeve 122 until a proximal end of the locking member 225 of the liner key is disposed proximally of a proximal-most end of the guide tube 223. As will be explained in greater detail below, the coupling sleeve 122 receives the liner key 221 within the coupling sleeve by sliding engagement in a first orientation, and rotation of the liner key 221 to a second orientation secures the key in the coupling sleeve restricting the key from distal movement out of the coupling sleeve. Therefore, in the illustrated embodiment, the liner key 221 is secured to the coupling sleeve 122 by rotational locking. In an embodiment, the coupling sleeve 122 centers the guide tube 223 within the buckle tube 71 which in turn centers and aligns the liner 14 within the drive coil 12. Thus, the liner 14 is prevented from being damaged by the drive coil 12 rotating around the liner.

In the illustrated embodiment, the coupling sleeve 122 comprises an elongate member having a generally cylindrical outer surface and an interior passage 172 having a generally rectangular shape defining four planar inner side surfaces 174. The interior passage 172 is configured to receive the locking member 225 of the liner key 221 when the liner assembly 224 is inserted into the coupling sleeve 122. In particular, the interior passage 172 receives the locking member 225 when the locking member is in the first rotational orientation whereby the cuboidal shape of the locking member is aligned with the rectangular shape of the interior passage (FIG. 12A). Once the liner key 221 is fully inserted into the coupling sleeve 122 such that an entirety of the locking member 225 is located proximally of the proximal-most end of the guide tube 223, the liner assembly 224 including the liner key 221 can be rotated through a partial rotation causing the locking member 225 to become misaligned with the interior passage 172 in the coupling sleeve 122 (FIGS. 12B and 12C). For example, the liner assembly 224 may be rotated between about 30 and about 40 degrees. It is envisioned that other degrees of rotation can be imparted on the liner assembly 224 without departing from the scope of the disclosure. However, it will be understood that the size of the passage 172 limits free rotation of the liner key 221 within coupling sleeve 122. In one embodiment, the liner key 221 engages interior side surfaces 174 of the coupling sleeve 172 to limit free rotation of the key within the coupling sleeve. The misalignment of the locking member 225 with the interior passage 172 causes corners of a distal end of the locking member to come into registration with a proximal end surface of the guide tube 223. Therefore, a distally directed force being exerted on the liner assembly 224 causes the distal end of the locking member 225 to engage the proximal end surface of the guide tube preventing the liner key from being pulled back out of the proximal end of the coupling sleeve 122. Thus, the partial rotation of the liner key 221 locks the liner key in place in the coupling sleeve 122. In the illustrated embodiment, rotation of the liner assembly 224 is caused by rotation of the drive coil 12 by the motor 43. Accordingly, the liner assembly 224 has a first orientation prior to rotation of the drive coil 12 to rotate the tissue-removing element 22 and a second orientation after rotation of the elongate body.

It will be understood that the coupling sleeve 122 could have other shapes without departing from the scope of the disclosure. For example, broadly, the coupling sleeve may have a non-circular or non-rounded exterior shape. In an embodiment, the coupling sleeve 122, guide tube 223, gearbox housing 55, and advancer frame 73 may be broadly considered a coupling assembly for coupling the liner assembly 224, including the inner liner 14, to the advancer 45.

Referring to FIGS. 1, and 3, the isolation sheath 22 comprises a tubular sleeve configured to isolate and protect a subject's arterial tissue within a body lumen from the rotating drive coil 12. The isolation sheath 22 is fixed to the handle 40 at a proximal end of the isolation sheath and does not rotate. The isolation sheath 22 provides a partial enclosure for the drive coil 12 and inner liner 14 to move within the isolation sheath. The inner diameter of the isolation sheath 22 is sized to provide clearance for the drive coil 12. The space between the isolation sheath 22 and the drive coil 12 allows for the drive coil to rotate within the isolation sheath and provides an area for saline perfusion between the isolation sheath and drive coil. The outer diameter of the isolation sheath 22 is sized to provide clearance with an inner diameter of a guide catheter (not shown) for delivering the catheter 10 to the desired location in the body lumen. In one embodiment, the isolation sheath 22 has an inner diameter of about 0.050 inches (1.27 mm), an outer diameter of about 0.055 inches (1.4 mm), and a length of about 1500 mm (59 inches). The isolation sheath 22 can have other dimensions without departing from the scope of the disclosure. In one embodiment, the isolation sheath 22 is made from Polytetrafluoroethylene (PTFE). Alternatively, the isolation sheath 22 may comprise a multi-layer construction. For example, the isolation sheath 22 may comprise an inner layer of perfluoroalkoxy (PFA), a middle braided wire layer, and an outer layer of Pebax.

Referring to FIGS. 1-3, the drive coil 12 may comprise a tubular stainless steel coil configured to transfer rotation and torque from the motor 43 to the tissue-removing element 20. Configuring the drive coil 12 as a coiled structure allows for the rotation and torque of the drive coil 12 to be applied to the tissue-removing element 20 when the catheter 10 is traversed across a curved path. The coil configuration of the drive coil 12 is also configured to expand its inner diameter when the coil is rotated so that the drive coil remains spaced from the inner liner 14 during operation of the catheter 10. In one embodiment, the drive coil 12 has an inner diameter of about 0.023 inches (0.6 mm) and an outer diameter of about 0.035 inches (0.9 mm). The drive coil 12 may have a single layer construction. For example, the drive coil 12 may comprise a 7 filar (i.e., wire) coil with a lay angle of about 30 degrees. Alternatively, the drive coil 12 could be configured from multiple layers without departing from the scope of the disclosure. For example, the drive coil 12 may comprise a base coil layer and a jacket (e.g., Tecothane™) disposed over the base coil layer. In one embodiment, the drive coil 12 comprises a 15 filar coil with a lay angle of about 45 degrees. The Tecothane™ jacket may be disposed over the base coil layer. Alternatively, the drive coil 12 may comprise a dual coil layer configuration with two coil layers which also includes an additional jacket layer over the two coil layers. For example, the drive coil may comprise an inner coil layer comprising a 15 filar coil with a lay angle of about 45 degrees, and an outer coil layer comprising a 19 filar coil with a lay angle of about 10 degrees. Drive coils 12 having other configurations are also envisioned.

Referring to FIGS. 1-3 and 13, the inner liner 14 comprises a multiple layer tubular body configured to isolate the guidewire 26 from the drive coil 12 and tissue-removing element 20. The inner liner 14 is extendable through the handle 40 from a position within the handle to a position distal of the handle. In one embodiment, the inner liner 14 is coupled to the components within the handle 40 but is not fixedly attached to the housing 41 to allow translation of the inner liner relative to the housing. The inner liner 14 has an inner diameter that is sized to pass the guidewire 26. The inner liner 14 protects the guidewire from being damaged by the rotation of the drive coil 12 by isolating the guidewire from the rotatable drive coil. The inner liner 14 may also extend past the tissue-removing element 20 to protect the guidewire 26 from the rotating tissue-removing element. Thus, the inner liner 14 is configured to prevent any contact between the guidewire 26 and rotating components of the catheter 10. Therefore, any metal-to-metal engagement is eliminated by the inner liner 14. This isolation of the drive coil 12 and tissue-removing element 20 from the guidewire 26 also ensures that the rotation of the drive coil and tissue-removing element is not transferred or transmitted to the guidewire. As a result, a standard guidewire 26 can be used with the catheter 10 because the guidewire does not have to be configured to withstand the torsional effects of the rotating components. Additionally, by extending the inner liner 14 through the tissue-removing element 20 and past the distal end of the tissue-removing element, the inner liner stabilizes the tissue-removing element by providing a centering axis for rotation of the tissue-removing element about the inner liner.

Figure 13:
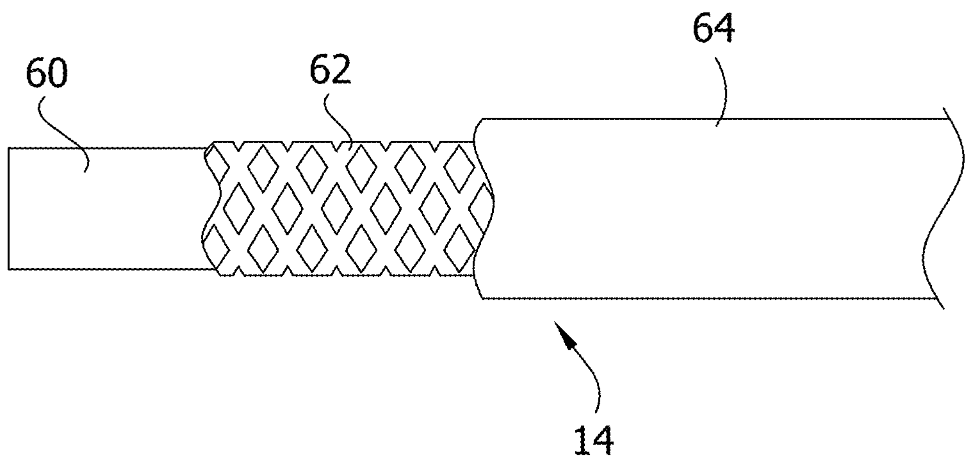
FIG. 13 is a fragmentary elevation of an isolation liner of the catheter with portions broken away to show internal details.

In the illustrated embodiment, the inner liner 14 comprises an inner PTFE layer 60, an intermediate braided layer 62 comprised of stainless steel, and an outer layer 64 of polyimide (FIG. 13). The inner PTFE layer 60 provides the inner liner 14 with a lubricous interior which aids in the passing of the guidewire 26 through the inner liner. The stainless steel intermediate braided layer 62 provides rigidity and strength to the inner liner 14 so that the liner can withstand the torsional forces exerted on the inner liner by the drive coil 12. In one embodiment, the intermediate braided layer 62 is formed from 304 stainless steel. The polyimide outer layer 64 provides wear resistance as well as having a lubricous quality which reduces friction between the inner liner 14 and the drive coil 12. Additionally, a lubricious film, such as silicone, can be added to the inner liner 14 to reduce friction between the inner liner and the drive coil 12. In one embodiment, the inner liner 14 has an inner diameter ID of about 0.016 inches (0.4 mm), an outer diameter OD of about 0.019 inches (0.5 mm), and a length of about 59 inches (1500 mm). The inner diameter ID of the inner liner 14 provides clearance for the standard 0.014-inch guidewire 26. The outer diameter OD of the inner liner 14 provides clearance for the drive coil 12 and tissue-removing element 20. Having a space between the inner liner 14 and the drive coil 12 reduces friction between these two components as well as allows for saline perfusion between the components. It will be understood that the inner liner 14 may have other configurations without departing from the scope of the disclosure.

Figure 14:
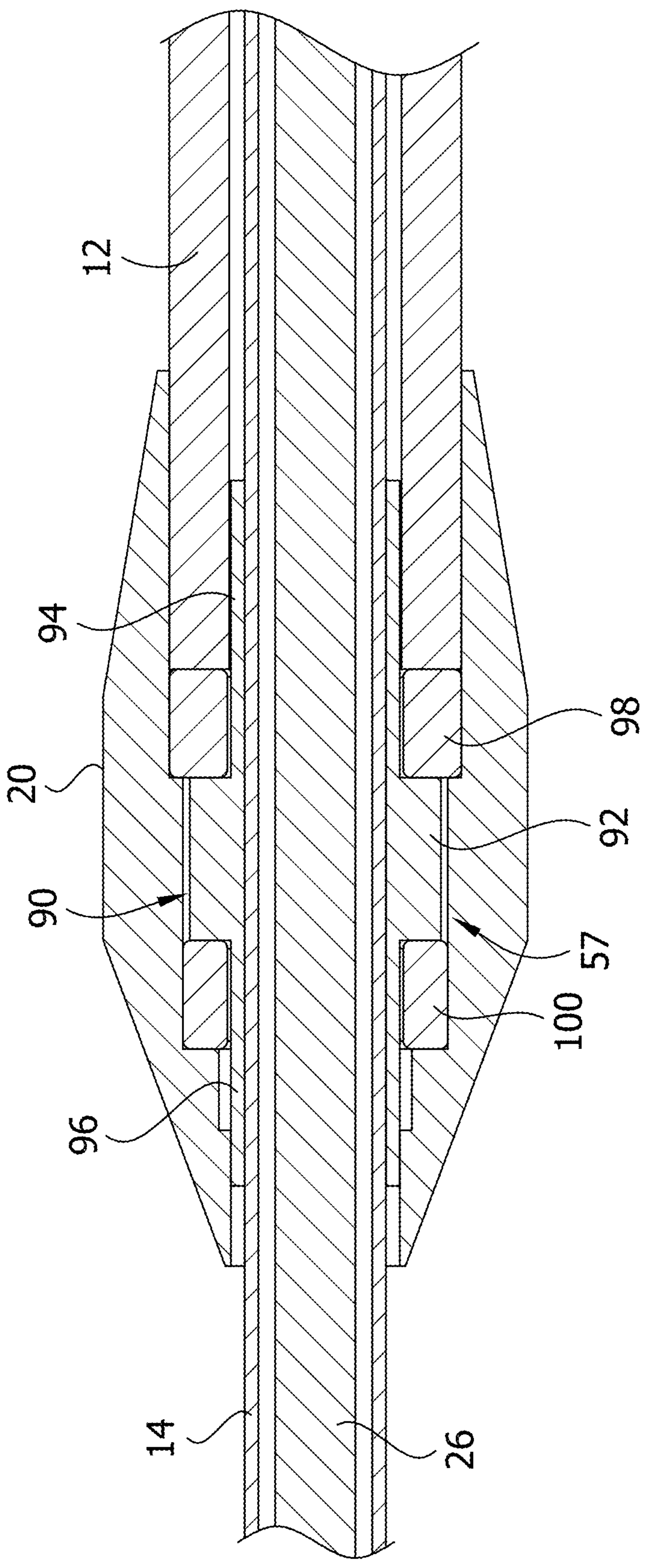
FIG. 14 is an enlarged fragmentary longitudinal cross section of the distal end portion of the catheter in FIG. 2.

Referring to FIGS. 1, 2, and 14, the tissue-removing element 20 extends along the longitudinal axis LA from a proximal end adjacent the distal end portion of the drive coil 12 to an opposite distal end. The tissue-removing element 20 is operatively connected to the motor 43 for being rotated by the motor. When the catheter 10 is inserted into the body lumen and the motor 43 is rotating the tissue-removing element 20, the tissue-removing element is configured to remove occlusive tissue in the body lumen to separate the tissue from the wall of the body lumen. Any suitable tissue-removing element for removing tissue in the body lumen as it is rotated may be used in one or more embodiments. In the illustrated embodiment, the tissue-removing element 20 comprises an abrasive burr configured to abrade tissue in the body lumen when the motor 43 rotates the abrasive burr. The abrasive burr 20 has an abrasive outer surface formed, for example, by a diamond grit coating, surface etching, or the like. In other embodiments, the tissue-removing element 20 can comprise one or more cutting elements having smooth or serrated cutting edges, a macerator, a thrombectomy wire, etc.

Figure 15:
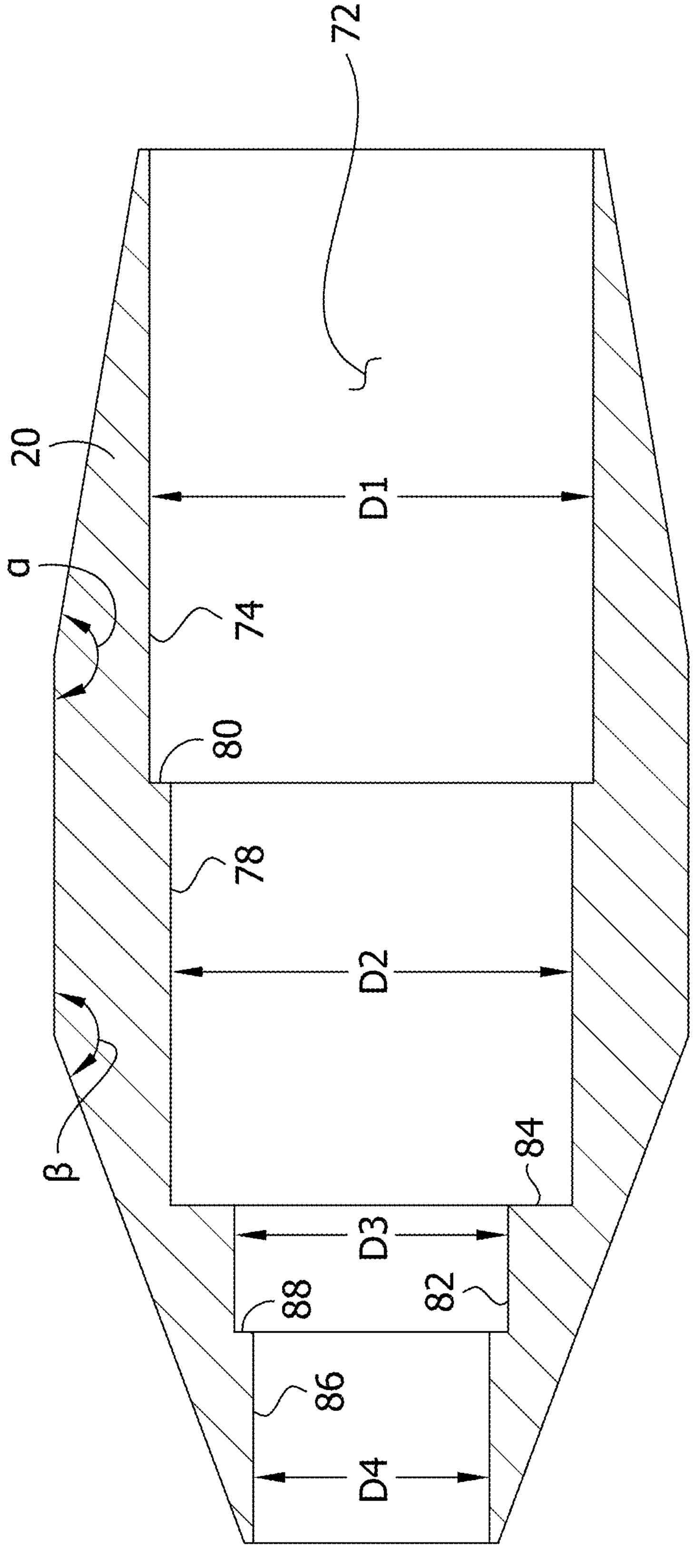
FIG. 15 is an enlarged longitudinal cross section of a tissue-removing element of the catheter.

Referring to FIG. 15, a cavity 72 extends longitudinally through the tissue-removing element 20 such that the tissue-removing element defines openings at its proximal and distal ends. The cavity 72 includes a first diameter portion 74 extending distally from the proximal end of the tissue-removing element 20 and a second diameter portion 78 extending distally from the first diameter portion forming a first shoulder 80 disposed between the first and second diameter portions. A third diameter portion 82 extends distally from the second diameter portion 78 and forms a second shoulder 84 between the second and third diameter portions. A fourth diameter portion 86 extends distally from the third diameter portion to the distal end of the tissue-removing element and forms a third shoulder 88 between the third and fourth diameter portions. The diameters of the first, second, third, and fourth diameter portions 74, 78, 82, 86 are constant along their lengths. In the illustrated embodiment, a diameter D1 of the first diameter portion 74 is larger than a diameter D2 of the second diameter portion 78, the diameter D2 is larger than a diameter D3 of the third diameter portion 82, and the diameter D3 is larger than a diameter D4 of the fourth diameter portion 86. In one embodiment, the diameter D1 of the first diameter portion 74 is about 0.037 inches (0.95 mm), the diameter D2 of the second diameter portion 78 is about 0.035 inches (0.9 mm), the diameter D3 of the third diameter portion 82 is about 0.033 inches (0.85 mm), and the diameter D4 of the fourth diameter portion 86 is about 0.031 inches (0.8 mm). Other cross-sectional dimensions are also envisioned without departing from the scope of the disclosure.

The inner liner 14 extends through the drive coil 12 and past the distal end of the tissue-removing element 20. The fourth diameter portion 86 of the cavity 72 is sized to pass the inner liner 14 with a small clearance. The inner diameter D4 provides clearance between the tissue-removing element 20 and the inner liner 14 to reduce friction between components. Accordingly, the tissue-removing element 20 is shaped and arranged to extend around at least a portion of the drive coil 12 and inner liner 14 and thus provides a relatively compact assembly for abrading tissue at the distal end portion 18 of the catheter 10.

Figure 16:
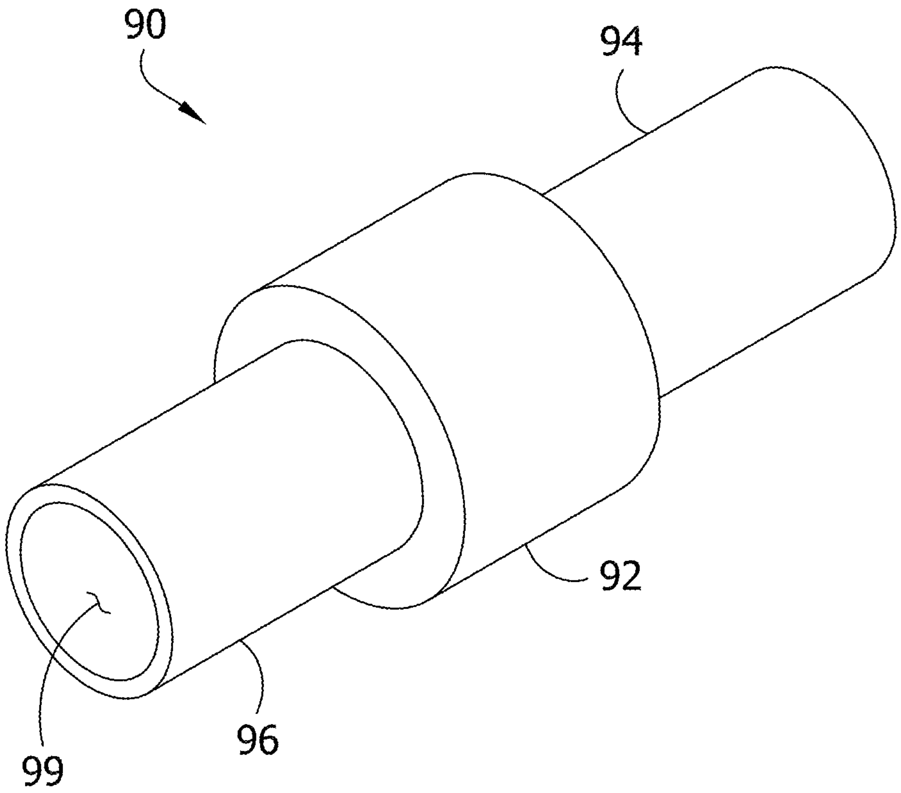
FIG. 16 is a perspective of a bushing of the catheter.

Referring to FIGS. 14-16, a bushing 90 is received in the cavity 72 of the tissue-removing element 20 and around the inner liner 14. The busing 90 comprises a center ring portion 92, a proximal ring portion 94 extending proximally from the center ring portion, and a distal ring portion 96 extending distally from the center ring portion. The ring portions of the bushing 90 define a channel 99 extending through the bushing that receives a portion of the inner liner 14. In the illustrated embodiment, the center ring portion 92 has a larger outer diameter than the proximal and distal ring portions 94, 96. The center ring portion 92 is disposed in the second diameter portion 78 of the cavity 72, the proximal ring portion 94 is disposed in the first diameter portion 74, and the distal ring portion 96 is disposed in the second and third diameter portions 78, 82. In one embodiment, the bushing 90 is made from polyetheretherketone (PEEK) and polytetrafluoroethylene (PTFE). However, the bushing 90 can be formed from other material without departing from the scope of the disclosure.

Figure 17:
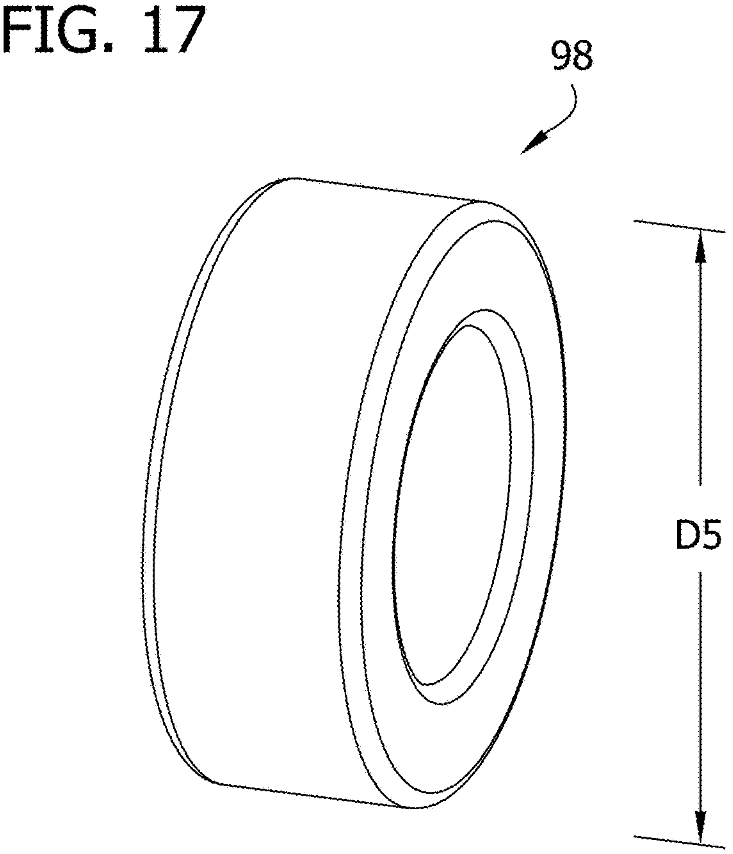
FIG. 17 is a perspective of a first bearing of the catheter.
Figure 18:
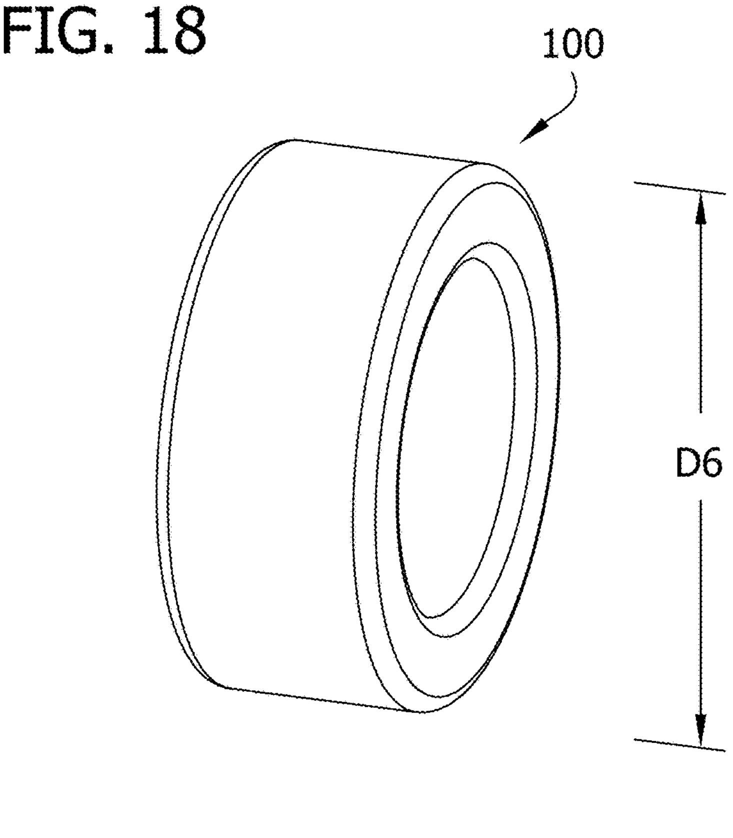
FIG. 18 is a perspective of a second bearing of the catheter.

Referring to FIGS. 14, 17, and 18, a first bearing 98 is disposed around the proximal ring portion 94 of the bushing 90, and a second bearing 100 is disposed around the distal ring portion 96 of the bushing. The first bearing 98 has an outer diameter D5 that is greater than an outer diameter D6 of the second bearing 100. In one embodiment, the first and second bearings 98, 100 are made from Zirconia. The first bearing 98 is disposed in registration with the first diameter portion 74 of the cavity 72 in the tissue-removing element 20 and is seated between a distal end of the drive coil 12 at a proximal end of the first bearing, and the center ring portion 92 of the bushing 90 and first shoulder 80 at a distal end of the first bearing. The second bearing 100 is disposed in registration with the second diameter portion 78 of the cavity 72 and is seated between the second shoulder 84 at a distal end of the second bearing, and the center ring portion 92 of the bushing 90 at a proximal end of the second bearing. As such the bushing 90 and the first and second bearings 98, 100 are held within the cavity 72 of the tissue-removing element 20. Broadly, the bushing 90 and the first and second bearings 98, 100 may be considered a coupling assembly 57 for coupling the inner liner 14 to the tissue-removing element 20.

Referring to FIG. 14, an interior surface of the bushing 90 is fixedly attached to the inner liner 14 such that the inner liner is coupled to the tissue-removing element 20 through the bushing. In one embodiment, an adhesive such as an epoxy glue bonds the bushing 90 to the inner liner 14. As such, the bushing 90 does not rotate around the inner liner 14. The drive coil 12 is directly and fixedly attached to the tissue-removing element 20. The tissue-removing element 20 can be fixedly attached to the distal end of the drive coil 12 by any suitable means. In one embodiment, adhesive bonds the drive coil 12 to the tissue-removing element 20. The drive coil 12 is received in the first diameter portion 74 of the cavity 72 and a distal end of the drive coil abuts the first bearing 98. However, the inner liner 14 is not directly attached to the tissue-removing element 20, and the drive coil 12 is not directly attached to the bushing 90, the first and second bearings 98, 100, or inner liner. Thus, rotation of the drive coil 12 and tissue-removing element 20 is not transmitted to the inner liner 14 to also rotate the inner liner. Rather the tissue-removing element 20 rotates around the bushing 90 and the first and second bearings 98, 100. And because the inner liner 14 is fixedly attached to the bushing 90, which is retained within the cavity 72 of the tissue-removing element 20 by the drive coil 12, the inner liner is coupled to the drive coil and tissue-removing element through the bushing and bearing arrangement.

With reference to FIG. 7, fixedly attaching the guide tube 223 to the gearbox housing 55 and attaching the gearbox housing to the distal end of the advancer frame 73 couples the liner assembly 224 to the advancer frame so that the liner assembly moves along with the advancer frame. Therefore, the inner liner 14 is configured to provide a push and pull force to the tissue-removing element 20 when the advancer 45 is moved relative to the handle 40. Accordingly, movement of the advancer 45 causes direct translational movement of the inner liner 14 which is then transmitted to the drive coil 12 and tissue-removing element 20. This configuration utilizes the structure of the inner liner 14 to transfer the push and pull force to the distal end of the catheter 10. The stiffness of the inner liner 14 is particularly suited to efficiently transfer the pushing and pulling force to the tissue-removing element 20. This also allows a more flexible drive coil 12 to be used.

Referring to FIGS. 1 and 2, to remove tissue in the body lumen of a subject, a practitioner inserts the guidewire 26 into the body lumen of the subject, to a location distal of the tissue that is to be removed. Subsequently, the practitioner inserts the proximal end portion of the guidewire 26 through the guidewire lumen 24 of the inner liner 14 and through the handle 40 so that the guidewire extends through the proximal port 47 in the handle. With the catheter 10 loaded onto the guidewire 26, the practitioner advances the catheter along the guidewire until the tissue-removing element 20 is positioned proximal and adjacent the tissue. When the tissue-removing element 20 is positioned proximal and adjacent the tissue, the practitioner actuates the motor 43 using the actuator 42 to rotate the drive coil 12 and the tissue-removing element mounted on the drive coil. The tissue-removing element 20 abrades (or otherwise removes) the tissue in the body lumen as it rotates. While the tissue-removing element 20 is rotating, the practitioner may selectively move the drive coil 12 and inner liner 14 distally along the guidewire 26 to abrade the tissue and, for example, increase the size of the passage through the body lumen. The practitioner may also move the drive coil 12 and inner liner 14 proximally along the guidewire 26, and may repetitively move components in distal and proximal directions to obtain a back-and-forth motion of the tissue-removing element 20 across the tissue by sliding the advancer 45 back and forth within the slot 186 in the handle 40. The practitioner is able to exercise a greater degree of control over the movement of the tissue-removing element 20 because coupling between the advancer 45 and the tissue-removing element 20 to transfer force from the advancer to the tissue-removing element is performed by the relatively stiff inner liner 14. Thus, there is no lost motion between the movement of the advancer 45 and the corresponding movement of the tissue-removing element 20. During the abrading process, the bushing 90 and first and second bearings 98, 100 couple the inner liner 14 to the tissue-removing element 20 and allow the drive coil 12 and tissue-removing-element to rotate around the inner liner. The inner liner 14 also isolates the guidewire 26 from the rotating drive coil 12 and tissue-removing element 20 to protect the guidewire from being damaged by rotating components. As such, the inner liner 14 is configured to withstand torsional and frictional effects of the rotating drive coil 12 and tissue-removing element 20 without transferring those effects to the guidewire 26. In an embodiment, the coupling of the inner liner 14 and tissue removing element 20 allows for movement of the inner liner, such as translational movement within the body lumen, to be transmitted to the drive coil 12 and tissue-removing element to move the drive coil and tissue-removing element through the body lumen with the inner liner. When the practitioner is finished using the catheter 10, the catheter can be withdrawn from the body lumen and unloaded from the guidewire 26 by sliding the catheter proximally along the guidewire. The guidewire 26 used for the abrading process may remain in the body lumen for use in a subsequent procedure.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:

an elongate body having an axis, and proximal and distal end portions spaced apart from one another along the axis, wherein the elongate body is sized and shaped to be received in the body lumen;

a handle mounted to the proximal end portion of the elongate body, the handle comprising a housing enclosing components operable to cause rotation of the elongate body;

a tissue-removing element mounted on the distal end portion of the elongate body, the tissue-removing element being configured to remove the tissue as the tissue-removing element is rotated by the elongate body within the body lumen;

a liner assembly defining a guidewire lumen, the liner assembly including an inner liner and a key fixedly attached to a proximal end of the inner liner, wherein the key has an exterior surface with a cross-sectional shape having sides intersecting at corners; and a coupling assembly including a coupling sleeve having an interior surface defining a passage with a cross-sectional shape corresponding to and larger than the cross-sectional shape of the exterior surface of the key, wherein the key is received in the coupling sleeve and is rotationally offset relative to the passage of the coupling sleeve such that the corners of the key engage sides of the interior surface to prevent the key from rotating relative to the coupling sleeve.

2. The tissue-removing catheter as set forth in claim 1, wherein the inner liner extends distally from the key and through the elongate body.

3. The tissue-removing catheter as set forth in claim 1, further comprising a guide tube attached to and extending distally from a distal end portion of the coupling sleeve, wherein the inner liner extends through the guide tube.

4. The tissue-removing catheter as set forth in claim 1, further comprising a motor in the handle and operatively engaging the elongate body for driving rotation of the elongate body and the tissue-removing element mounted on the elongate body.

5. The tissue-removing catheter as set forth in claim 4, further comprising a gearbox housing at least partially enclosing a gear assembly operatively connected to the motor.

6. The tissue-removing catheter as set forth in claim 5, further comprising a guide tube, wherein a proximal end of the guide tube is attached to the coupling sleeve and a distal end of the guide tube is attached to the gearbox housing.

7. The tissue-removing catheter as set forth in claim 6, wherein the guide tube is fixedly attached to the gearbox housing.

8. The tissue-removing catheter as set forth in claim 6, further comprising a buckle tube in the handle, wherein the coupling sleeve is received in the buckle tube in a non-rotational, sliding engagement.

9. The tissue-removing catheter as set forth in claim 8, further comprising a guidewire port mounted on a proximal end of the buckle tube.

10. The tissue-removing catheter as set forth in claim 1, wherein the inner liner is coupled to the tissue-removing element at a distal end portion of the inner liner.

11. The tissue-removing catheter as set forth in claim 1, wherein the inner liner is free of direct attachment to the tissue-removing element.

12. The tissue-removing catheter as set forth in claim 1, further comprising an advancer mounted on the handle and movable relative to the housing, the liner assembly being coupled to the advancer such that movement of the advancer causes a corresponding movement of the inner liner to exert a push force on the tissue-removing element to advance the tissue-removing element and a pull force on the tissue-removing element to retract the tissue-removing element for moving the tissue-removing element relative to the handle.

13. The tissue-removing catheter as set forth in claim 3, wherein the liner assembly is configured to engage a proximal end of the guide tube to inhibit distal movement of the liner assembly relative to the guide tube.

14. The tissue-removing catheter as set forth in claim 1, wherein the key includes a locking member having the exterior surface with a cross-sectional shape having sides intersecting at corners.

15. The tissue-removing catheter as set forth in claim 14, wherein the key further includes an extension member extending distally from the locking member, wherein the inner liner is secured within the extension member.

16. A method of assembling the tissue-removing catheter as set forth in claim 1, the method comprising:

aligning the key with the passage of the coupling sleeve;

inserting, after said aligning, the key into the passage of the coupling sleeve; and rotating the key about a longitudinal axis of the key relative to the coupling sleeve so that the corners of the key engage sides of the interior surface to prevent the key from further rotating relative to the coupling sleeve.

* * * * *